United States Patent
Townsend et al.

(10) Patent No.: US 6,834,436 B2
(45) Date of Patent: Dec. 28, 2004

(54) POSTURE AND BODY MOVEMENT MEASURING SYSTEM

(75) Inventors: Christopher P. Townsend, Shelburne, VT (US); Steven W. Arms, Williston, VT (US)

(73) Assignee: MicroStrain, Inc., Williston, VT (US)

(*) Notice: Subject to any disclaimer, the term of this patent is extended or adjusted under 35 U.S.C. 154(b) by 19 days.

(21) Appl. No.: 10/082,562

(22) Filed: Feb. 23, 2002

(65) Prior Publication Data

US 2002/0170193 A1 Nov. 21, 2002

Related U.S. Application Data

(60) Provisional application No. 60/271,090, filed on Feb. 23, 2001.

(51) Int. Cl.[7] .................................................. G01B 1/00
(52) U.S. Cl. ......................... 33/512; 33/341; 600/301; 482/8
(58) Field of Search ...................... 33/512, 365, 366.11, 33/366.12, 366.13, 366.14, 366.25, 366.26, 370–373, 340–343, 347; 600/301; 482/8

(56) References Cited

U.S. PATENT DOCUMENTS

| | | | | |
|---|---|---|---|---|
| 4,757,453 A | * | 7/1988 | Nasiff ........................ | 73/379.01 |
| 5,375,610 A | * | 12/1994 | LaCourse et al. ............ | 600/595 |
| 5,390,104 A | * | 2/1995 | Fulton .......................... | 700/65 |
| 5,459,676 A | * | 10/1995 | Livingston .................. | 700/296 |
| 5,477,953 A | * | 12/1995 | Powell et al. ............... | 194/209 |
| 5,593,431 A | * | 1/1997 | Sheldon ....................... | 607/19 |
| 6,059,576 A | * | 5/2000 | Brann ........................ | 434/247 |
| 6,066,075 A | * | 5/2000 | Poulton ........................ | 482/8 |
| 6,165,143 A | * | 12/2000 | van Lummel ............... | 600/595 |
| 6,198,394 B1 | * | 3/2001 | Jacobsen et al. ......... | 340/573.1 |
| 6,210,301 B1 | * | 4/2001 | Abraham-Fuchs et al. ..... | 482/8 |
| 6,305,221 B1 | * | 10/2001 | Hutchings .................... | 73/488 |
| 6,323,807 B1 | * | 11/2001 | Golding et al. ............. | 342/419 |
| 6,447,425 B1 | * | 9/2002 | Keller et al. .................. | 482/8 |
| 2002/0091482 A1 | * | 7/2002 | Eakle et al. ................ | 701/207 |

* cited by examiner

*Primary Examiner*—Christopher W. Fulton
*Assistant Examiner*—Amy R. Cohen
(74) *Attorney, Agent, or Firm*—James Marc Laas

(57) ABSTRACT

A sensing device is attached to a living subject that includes a first sensors for distinguishing lying, sitting, and standing positions. In another embodiment, sensor data is stored in a storage device as a function of time. Multiple points or multiple intervals of the time dependent data are used to direct a feedback mechanism to provide information or instruction in response to the time dependent output indicating too little activity, too much time with a joint not being moved beyond a specified range of motion, too many motions beyond a specified range of motion, or repetitive activity that can cause repetitive stress injury.

44 Claims, 10 Drawing Sheets

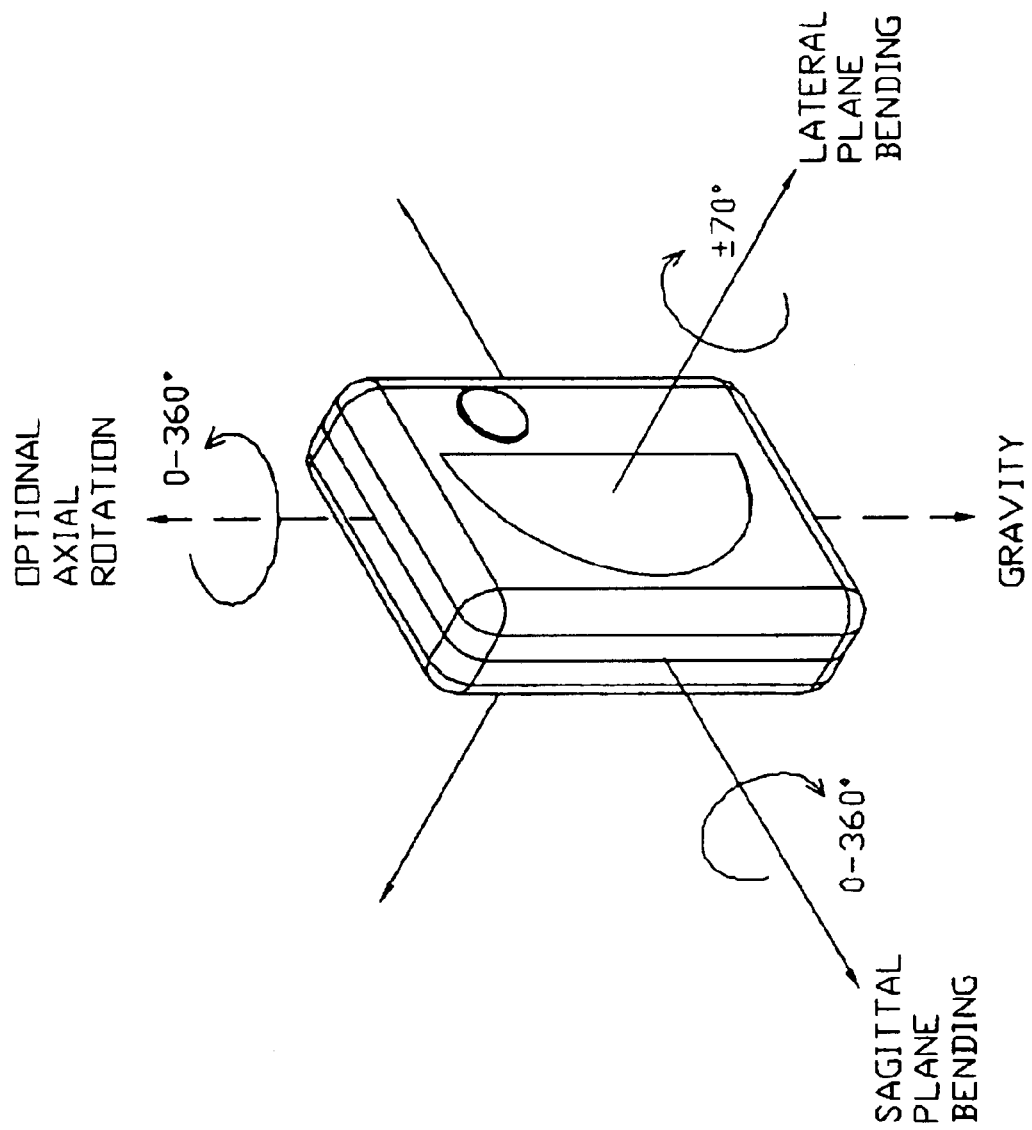

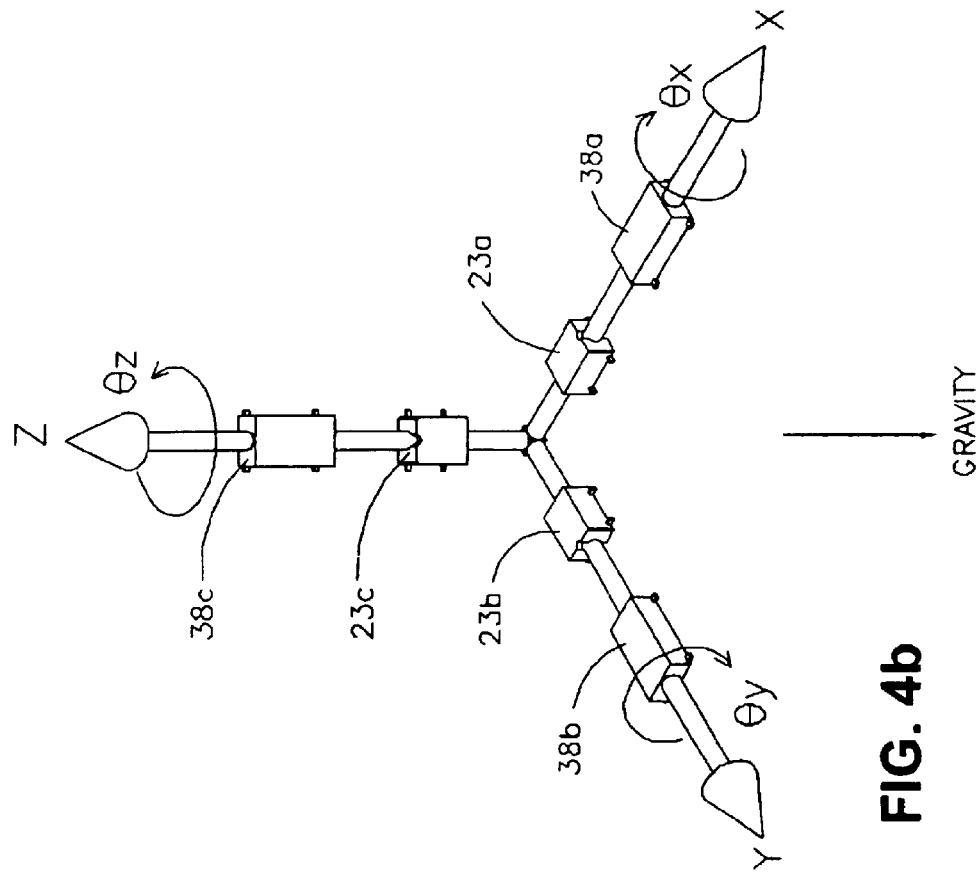

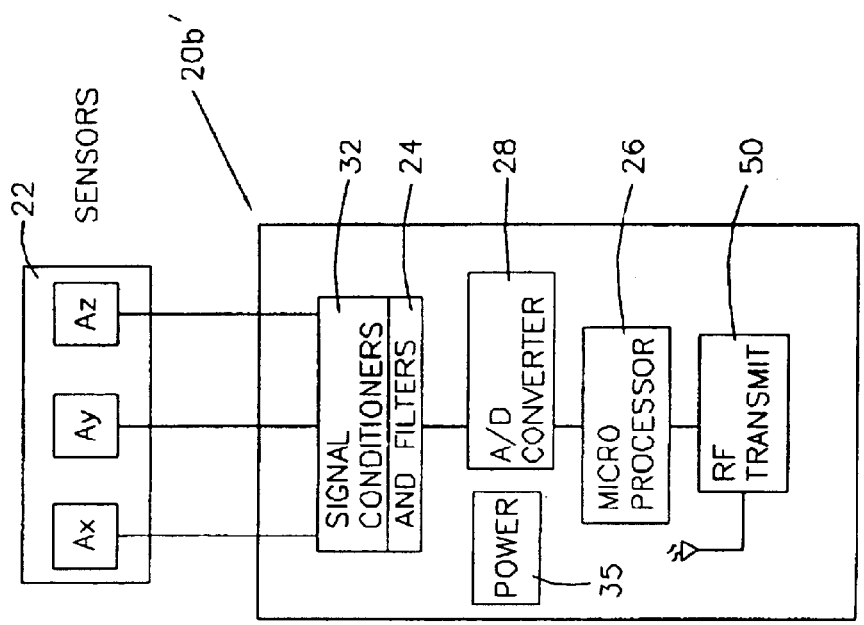
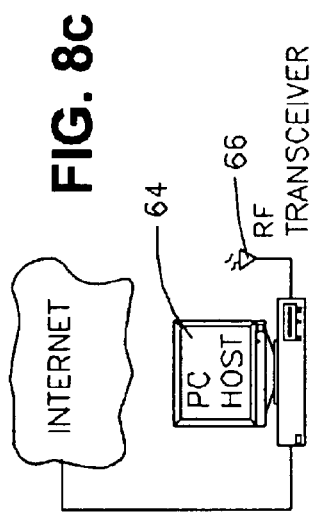
FIG. 8a
FIG. 8b
FIG. 8c

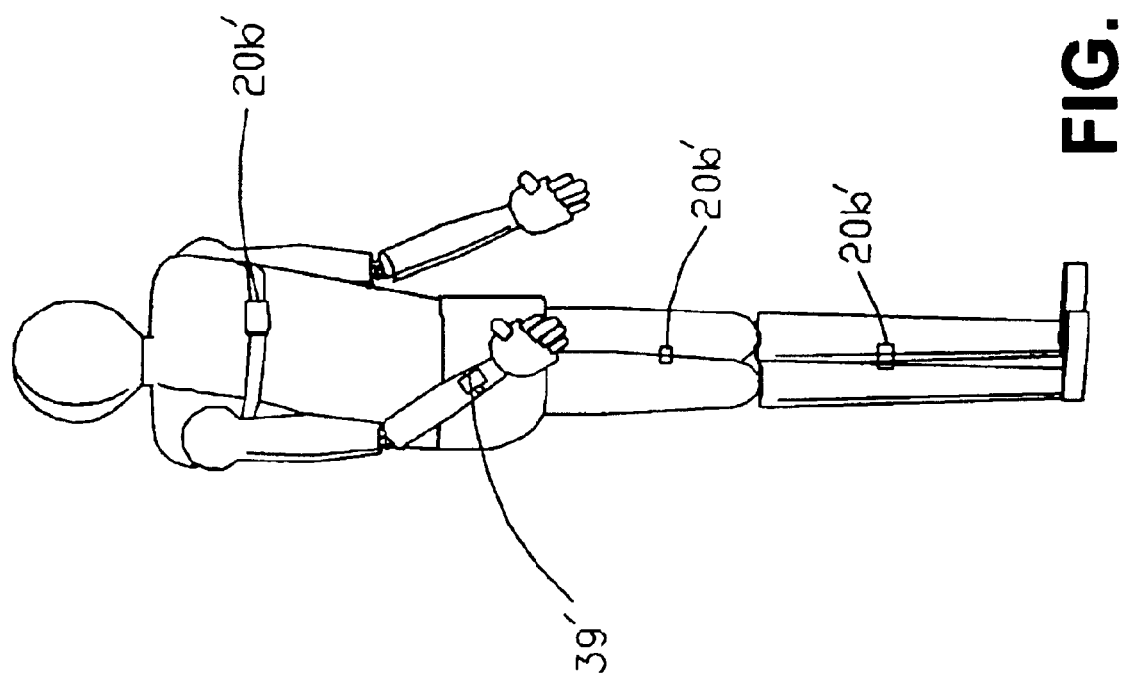

POSTURE AND BODY MOVEMENT MEASURING SYSTEM

RELATED APPLICATION

This application claims benefit of provisional U.S. patent application No. 60/271,090, filed Feb. 23, 2001.

FIELD OF THE INVENTION

This invention generally relates to sensors. More particularly, it relates to a system for making measurements concerning posture, orientation, and movement. Even more particularly, it relates to a system for measuring posture or repetitive motion and providing feedback.

BACKGROUND OF THE INVENTION

The range of motion of a joint of the body may be restricted as a result of injury. Range of motion can increase with therapy, exercise, and healing. Measurement of range of motion is important in evaluating the extent of injury and progress toward healing.

On the other hand treatment of various injuries may require temporary restriction in the range of movement, and devices such as casts, braces, elastic bandages, and corsets have been used to provide such temporary restraint. Some of these devices and some ergonomic chairs have also been used to promote a more erect posture.

Electronic sensors have been developed to measure angles between body segments and to measure range of motion of various joints, as described in commonly assigned U.S. patent application Ser. No. 08/990,912 to Arms, ("the '912 patent application"), filed on Dec. 15, 1997, and incorporated herein by reference. The '912 patent application describes a pair of housings that contain a pair of inclinometer board assemblies and the cable and plugs for their connection. The inclinometer board assemblies each include pairs of accelerometers oriented orthogonal to each other, a/d converters, a multiplexer, a voltage regulator, and a microprocessor. The microprocessor computes the angle of each inclinometer housing with respect to the other.

Commonly assigned U.S. patent application Ser. No. 09/457,493 to Arms, ("the '493 patent application"), filed on Dec. 8, 1999, and incorporated herein by reference discloses an inclinometer that includes three orthogonal accelerometers and three orthogonal magnetometers used to measure earth's gravitational and magnetic field vectors from which pitch, roll, and yaw (compass heading) are calculated. Low pass filters are provided to minimize effects due to inertial inputs to the accelerometers that might interfere with accuracy. The invention also provides a digital network to allow multiple devices to be wired together on a single bus, a feature useful for applications, such as posture monitoring.

Mechanical and electronic sensors have been developed to measure range of motion, as described in U.S. Pat. No. 4,665,928 to Linial et al. Other devices, such as those described in U.S. Pat. No. 4,958,145 to Morris, U.S. Pat. No. 5,089,808 to Amirdash, and U.S. Pat. No. 5,128,655 to Shore use measurement devices that detect whether an incline angle has been exceeded and provide an alarm when the user exceeds that prescribed angle.

Restraint on the extent of movement with the ability to perform exercises within a prescribed range is provided in U.S. Pat. No. 5,823,975 to Stark, et al. An orthopaedic restraining device is provided which provides restraint while permitting a range of exercise during rehabilitation. A communications device is included to provide feedback to the prescribing physician so the physician can evaluate the patient's progress in regard to the exercise the physician prescribed. The device is equipped to summon the patient to perform exercise with a visual alarm or a vibrator, to verify that torque used for the exercise is within a prescribed limit, to provide choices of torque and repetitions for each exercise, and otherwise give the patient immediate feedback respecting exercise. For example, the control program calculates the work or energy exerted by the patient and displays the energy exerted as a percentage of the targeted energy amount.

U.S. Pat. No. 5,593,431, to Sheldon, "the '431 patent," determines the physical posture of a patient's body in relation to earth's gravitational field. A device with two or three DC accelerometers having sensitive axes mounted orthogonally within an implantable housing is adapted to be implanted with the sensitive axes generally aligned with the patient's body axes. The activity and body position signals from these sensors may be stored and/or used to monitor and effect the delivery of a therapy to the patient, e.g. by controlling the pacing rate of a rate responsive pacemaker. The device provides a multi-axis, solid state position and activity sensor operable along at least two orthogonal axes to distinguish the posture or positional attitude of the patient at rest and at levels of exercise.

However, the present inventors found that while the device of the '431 patent can distinguish various lying down positions from each other and from standing, the device cannot distinguish between various upright positions. For example, the device of the '431 patent cannot distinguish sitting from standing positions of the patient. Thus, a better system for monitoring is needed that provides improved ability to distinguish posture and activity in upright positions, and this solution is provided by the following invention.

SUMMARY OF THE INVENTION

It is therefore an object of the present invention to provide a device that can distinguish lying down, sitting and standing positions of a user;

It is a further object of the present invention to provide a device that distinguishes various postures within the sitting position;

It is a farther object of the present invention to provide a device that recognizes too much time in a kyphotic posture and prompts the user to spend more time in lordosis.

It is a further object of the present invention to provide notice or instruction indicating too much time in a fixed position or too much time with little activity;

It is a further object of the present invention to provide notice or instruction indicating repetitive activity that can cause repetitive stress injury;

It is a feature of the present invention to provide a plurality of sensors extending on each side of a hip joint to distinguish lying, sitting and standing positions;

It is a feature of the present invention to provide a plurality of sensors, a processor, a storage device, and a feedback mechanism, wherein the sensors provide a dc response to detect inactivity or too little activity;

It is an advantage of the present invention that the device provides warning of too much time in a kyphotic posture;

It is an advantage of the present invention that the device provides warning of too little activity or repetitive activity that can cause repetitive stress injury.

These and other objects, features, and advantages of the invention are accomplished by a device for attaching to a living subject, comprising a sensor, a processor, and a storage device. The sensor comprises an acceleration measurement device. Data from the sensor is processed in the processor and stored in the storage device for determining when a person is in a sitting position and for determining body posture in the sitting position.

Another aspect of the invention is accomplished by a device comprising a sensor, a processor, a storage device, and a feedback notifier. Data from the sensor is processed in the processor to provide an output. The output is stored in the storage device as a function of time. Multiple points of the time dependent output stored in the storage device are processed in the processor. The processor directs the feedback notifier to provide information or instruction in response to the time dependent output indicating too little activity or indicating repetitive activity that can cause repetitive stress injury.

BRIEF DESCRIPTION OF THE DRAWINGS

The foregoing and other objects, features, and advantages of the invention will be apparent from the following detailed description of the invention, as illustrated in the accompanying drawings, in which:

FIG. 3 is a three dimensional sensor unit of the present invention showing rotation around the orthogonal axis including the direction of the gravity vector;

FIG. 4a are equations to used calculate the accelerations and the angular positions of the sensor;

FIG. 4b show the accelerometers and magnetometers as they are ideally positioned along orthogonal axis and rotations around those axes;

FIG. 4c are equations to used calculate the components of earth's magnetic field and the rotation of the sensor about the z axis;

FIG. 8a is a block diagram of a wireless apparatus of the present invention;

FIG. 8b is a block diagram of a remote processing unit of the present invention; and FIG. 8c is a schematic diagram of a PC host system for communicating with the sensor module system or remote processing unit of the present invention; and FIG. 9 is a three dimensional view of a person using a wireless apparatus of the present invention having multiple sensor systems and a wrist mounted remote processing unit.

DETAILED DESCRIPTION OF THE INVENTION

Figure 1:
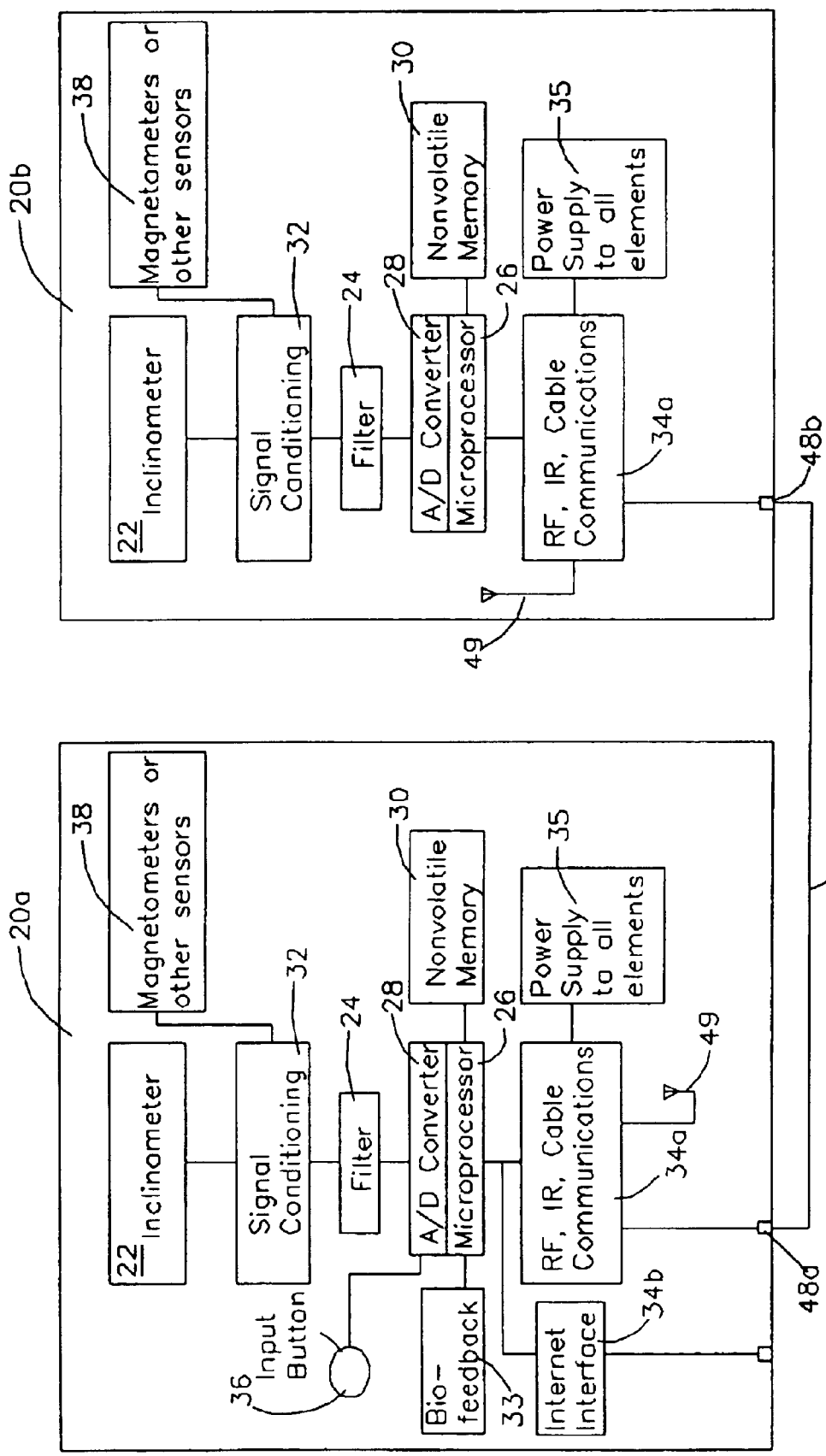
FIG. 1 is a block diagram of the sensor unit of the present invention.

The present inventors recognized that available accelerometer based posture monitors could not distinguish between lying down and each upright position of sitting and standing. The '431 patent, for example, distinguishes among several lying down positions but has no mechanism to distinguish sitting from standing. In addition, the present inventors recognized that physical discomfort and medical problems arising from posture and repetitive movements can be prevented with appropriate characterization and feedback. They recognized a common solution for a variety of problems, such as (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a job lifting boxes.

The present inventors designed a miniature electronic device that records position and posture within that position data over time, senses the circumstances that could lead to physical problems by analysing position and posture data over time, and signals the user to take action to avoid injury. The same equipment can also be used during physical therapy to monitor movements and exercises to ensure that a prescribed range of motion is not exceeded and to encourage proper performance of prescribed exercises. It can also be used to analyse movement during participation in physical activity, such as a sport involving a swing, to improve performance.

In one embodiment, the present invention networks a pair of angular position sensors, one on each side of the hip joint, to distinguish lying down, sitting, and standing positions. In another embodiment, the present invention repeatedly records position and/or posture data over time. Feedback is provided when a condition is met, such as position remains constant for too long a period of time or posture is kyphotic for too long a period of time. Feedback can also be provided if a repetitive stressful movement is repeated too many times or if a desired range of motion limit is exceeded too many times. Feedback can take the form of a vibration or an audible signal.

The present inventors recognized that there are three components to human energy expenditure in non-exercising subjects; basal metabolic rate (BMR), thermic effect of food (TEF) and non-exercise activity thermogenesis (NEAT). BMR is the rate at which energy is expended when an individual is laying down at rest in the postabsorptive state. In sedentary individuals it accounts for approximately 60% of total daily energy expenditure (TDEE) and is highly predicted by lean body mass within and across species, as described in a paper "Avian basal metabolic rates: their association with body composition and energy expenditure in nature," by S. Daan, D. Masman, and A. Groenewold, *Am J Physiol,* 1990;259(2 Pt 2):R333–40, and in a paper "Some consequences of body size," by L. E. Ford, *Am J Physiol,* 1984;247(4 Pt 2):H495–507. TEF is the increase in energy expenditure associated with the digestion, absorption, and storage of food and accounts for approximately 10% of TDEE. Several investigators believe TEF to represent a fixed proportion of TDEE, as described in a paper, "Human energy expenditure in affluent societies: an analysis of 574 doubly-labeled water measurements." by A. E. Black, W. A. Coward, A. M. Prentice, and T. J. Cole, *Eur J Clin Nutr,* 1996;50(2):72–92 and to be the invariant energy cost of converting food to metabolic fuels, as described in a paper, "Meal size and thermic response to food in male subjects as a function of maximum aerobic capacity," by J. O Hill, S. B. Heymsfield, C. D. McMannus, and M. DiGirolamo, *Metabolism,* 1984;33(8):743–9, and in a paper, "Thermic effect of food in lean and obese men," by D. A. Alessio, E C Kavle, M A Mozzoli, et al., *J Clin Invest*, 1988;81(6):1781–9 whereas others propose that TEF is actively regulated in response to changing food intake, as described in a paper, "Independent effects of obesity and insulin resistance on postprandial thermogenesis in men," by K R Segal J Albu, A Chun, A Edano, B Legaspi, and F X Pi-Sunyer, *J Clin Invest.* 1992;89(3):824–33.

NEAT is the thermogenesis that accompanies physical activities other than volitional exercise, such as the activities of daily living, such as sitting, standing and walking, body movement plus fidgeting, spontaneous muscle contraction, and maintaining posture when not recumbent. It accounts for approximately 30% of TDEE.

In one study published in a paper, "Assessment of the heart-rate method for determining energy expenditure in man, using a whole-body calorimeter," by M. J. Dauncey and W. P. James, published in *Br J Nutr,* 1979;42(1):1–13, the energy expenditure associated with lying, sitting and standing was measured in eight men confined to a room calorimeter. Total energy expenditure increased by 10% when seated compared to lying and by 36% when standing compared to lying. Furthermore, when these subjects were allowed to make voluntary movements to resemble fidgeting, energy expenditure increased further by 26±(SD) 11% in the lying position, 17±16% in the sitting position, and by 27±14% in the standing position. This experiment and others consistently demonstrate that low grade activities such as walking at ≈2 mph or cycling at 50W is associated with 2–3 fold increases in energy expenditure (7,9,10). Furthermore, the number of hours spent per day performing these activities can be added up so that the contribution of NEAT activities to total daily energy expenditure in free living, sedentary subjects can be clarified (FIG. 1). Thus, NEAT not only accounts for many hours in each day (in fact, in sedentary individuals,all hours spent awake, not resting and not eating) but the thermogenesis associated with each of these components is sufficiently great that NEAT has the potential to contribute significantly to total energy expenditure. The substantial majority of NEAT is accounted for by identifiable components such as body movement, sitting, standing and walking; fidgeting (small, non-purposeful distal limb movements) also contribute to NEAT.

A paper, "Role of nonexercise activity thermogenesis in resistance to fat gain in humans," by J. A. Levine, N. L. Eberhardt, and M. D. Jensen, published in *Science,* 1999; 283(5399):212–4, concludes that increases in NEAT predict resistance to fat gain with over-feeding. However, investigations into the mechanism of this effect are hampered by the limited information regarding the components of NEAT in free-living subjects.

The present inventors recognized that there is a large potential market for "smart" wearable instruments capable of comprehensive recording of human activity, body position, and energy expenditure is available. For example, approximately 800 obese patients are treated each year by the nutrition clinic of the Mayo Clinic. In the present invention, such patients would be allowed to keep their monitors of the present invention, and an infrastructure for remote data access over the internet over a secure server would allow clinicians, therapists, and personal trainers to improve their knowledge of each patient's activity level and compliance with treatment regimen.

Previously existing wearable monitors based on dynamic acceleration have not been able measure NEAT, since their outputs drop to zero when the subject stops moving. Heart rate monitors cannot measure NEAT reliably, since they also do not reflect the body's position or posture. However, the present inventors have provided instrumentation to overcome this difficulty. The instrument developed by the present inventors provides body position and posture, and provides information regarding slow movements of the body that can be correlated with NEAT.

The present inventors designed a comprehensive instrument to measure human activity and body position and to detect the contributions of sitting, standing, walking and fidgeting thermogenesis to NEAT. The instrument distinguishes and measures bouts of exercise as well as contributions from normal sedentary life. The instrument provides feedback to the wearer. This device can thus be used to modify human activities, and therefore has the potential to affect an individual's weight and posture.

A preliminary version of the device with a single sensor unit for placement on one body segment was evaluated in a paper,"Evaluation of Biofeedback Device in Reducing Pain and Improving Function of Individuals with Low Back Pain," by Krag, M. H., Fox, J. R., and McDonald, L. P.: published in *Rehabilitation Society of N. America*, Pittsburgh, Pa., 1997. The authors showed that wearing this device can result in more erect trunk postures which may result in reduced loads on the supporting muscles of the spine. Results of tests with the device were described in a paper, "Oh, My Aching Back", by Wolkomir, R., published in Smithsonian Magazine, pages 38–48, August, 1998.

The measurement of spinal curvature may prove useful, especially in applications where prolonged static standing and/or sitting may be encountered. Various scientific studies have documented that a prolonged seated posture, especially without proper lower back support, is detrimental to those who suffer from low back pain. Devices to monitor curvature of the spine during prolonged sitting have been developed. Such a "lordosimeter" typically includes a thin, flexible, polymeric or metallic strip or strips embedded within or covered by compliant materials. It may be placed comfortably along the spine using elastic straps. The thin, flexible strip typically includes one or more strain gauges such as bonded foil types, piezo-resistive, inductive, capacitive, or fiber optic. The strain gauge converts the bending of the strip as posture changes into an electrical signal indicative of spinal curvature. An example of these fiber optic curvature sensing devices is described in U.S. Pat. No. 5,321,257, incorporated herein by reference, and the devices are available from Measurand, Inc., Fredericton, NB, Canada.

In the present invention, output data of the lordosimeter providing spinal curvature is logged continually. The unit is programmed to provide feedback to the user if the user remains in a poor posture for too long a time. The unit is also programmed to warn the user if he or she remains in any static position for too long a time. Thus, the unit encourages the user to move around frequently and to avoid poor posture. The feedback can enhance the user's awareness of his or her posture. In addition, information about trunk inclination and orientation from measurements taken over a period of time can help determine what posture or movements are related to back pain.

In addition to monitoring position and posture, with biofeedback, wearable instruments could also enhance patient compliance with prescribed rehabilitation/exercise programs after a back injury or a spine surgery or during rehabilitation of injuries to other parts of the body.

A paper, "The Biomechanics of Low Back Injury: Implications on Current Practice in Industry and the Clinic," by S. M. McGill, published in *J. Biomechanics*, Vol. 30, No. 5, pp. 465–475, 1997, suggests that changing the body's position can alleviate joint pain and joint problems associated with overuse. Overuse injuries have risen in recent years, partly due to the increased time spent using computers, where the operator may infrequently change position and posture at the keyboard, as described in "OSHA—Its Role in the American Workplace" by R. Ferrante, executive producer, reported on National Public Radio by Robert Edwards, NPR's morning edition, Apr. 4$^{th}$, 1996.

The instrument developed by the present inventors is a wearable trainer or coach or personal tarnaguchi device that reminds its owner to change position, get up, walk, stretch, or vary activities that overuse a joint. The instrument logs data concerning the user's time history of activity, position, posture, movements, and the device can test for compliance with programmed goals. A built-in display may provide cues and/or a composite health score based on the recorded data. These capabilities could not only benefit those persons who are recovering from an injury, they could also prevent overuse related injuries.

In addition, the data gathered from the device of the present invention would be valuable to researchers and to companies who employ individuals who may be at risk for overuse injuries, including package handlers, meat packers, movers, athletes, computer users, elderly persons, etc. Wearable activity, position, and posture instruments could be also be used to record patient compliance with prescribed exercise and could proactively prompt the patient to perform prescribed activities to result in improved outcomes.

MicroStrain, Inc. designed and has long been marketing wearable dataloggers for tracking truck inclination with biofeedback through a vibrating pager enclosure, termed the Virtual Corset. These devices run for approximately six weeks using a single AA size battery. Data are recorded in an on-board non-volatile memory and can be downloaded via a connection to the serial port of a personal computer. Inclination is measured using a triaxial array of orthogonal static & dynamic response accelerometers. Preferably the inclinometer has capability to measure 360 degrees about at least one axis, as provided in a sensor available from Microstrain, Inc. called FAS-A. Even more preferably the inclinometer has capability to measure 360 degrees about two axes, which can be accomplished by providing three orthogonal accelerometers for each device attached to a body segment. For example, for measurement's of a person's torso, such a device provides measurements of flexion/extension (forward and backward bending) and lateral bending (sideways bending).

To also measure rotation of the body about an axis along the gravity vector one can also include three orthogonal magnetometers along with the three orthogonal accelerometers, as described in a paper, "A Miniature, Sourceless, Networked, Solid State Orientation Module", by Townsend, C. P., Guzik, D. C., Arms, S. W., published in the 9$^{th}$ *International Conference on Adaptive Structures & Tech.* (ICAST), Cambridge, Mass., October 1998, ("the ICAST paper"), and in a patent application Ser. No. 10/447,384. This device is is available from Microstrain, Inc. and is called 3DM.

In order to detect and distinguish body position, such as standing, sitting, and lying down, the present inventors found that a second sensor unit was needed. The present invention networks a pair of angular position sensors, one on each side of the hip joint, to distinguish the three positions. It uses a networked array of angular position sensors termed 3DM's, as described in commonly assigned U.S. patent application Ser. No. 09/457,493, incorporated herein by reference. The idea of networking sensors is also mentioned in the above mentioned ICAST paper by Towsend.

To also measure angular rotation about an axis, including angular rotation of a body and twist of a joint about the axis, the present inventors found that a second sensor unit was needed, one on each side of the joint. The sensor unit preferably provides 3 accelerometers and three magnetometers, such as the 3DM device of Microstrain, Inc., as described in the ICAST paper by Townsend. The joint can be the ankle, the knee, the hip, spine, neck, shoulder, elbow, or wrist. For example, for measuring axial rotation or twisting of the spine in a standing posture, one 3DM is mounted to the lower spine around the pelvis and the other is mounted to the upper body around the chest.

It is worth noting that for a subject in a lying down posture axial rotation of the spine can be measured with gravity referenced devices alone, without magnetometers, but gravity referenced devices cannot be used for such measurements when in a standing posture.

The present invention links a triad of dynamic and static response accelerometers and a triad of magnetometers attached to a thigh and similar triads attached to the torso. The magnetometers provide absolute rotational position about an axis coincident with Earth's gravity vector (compass heading, or yaw). Network capability is provided by an RS-485 connection between the sensors. The apparatus of the invention was tested on subjects who were standing, sitting, and lying, and the results show that accelerometer outputs from sensors on thigh and torso were easily able to distinguish the three positions, as shown in Table 1.

TABLE 1

Voltage outputs from inclinometers applied to the thigh and torso to detect standing, sitting and lying in three adults. Data are the mean of ten repetitions ± SD.

| | Subject | | | | | |
|---|---|---|---|---|---|---|
| | 1 Thigh | 1 Torso | 2 Thigh | 2 Torso | 3 Thigh | 3 Torso |
| Standing | 0.78 ± 0.01 | 0.88 ± 0.03 | 0.84 ± 0.01 | 0.91 ± 0.04 | 0.80 ± 0.01 | 0.98 ± 0.03 |
| Sitting | 4.00 ± 0.04 | 0.93 ± 0.05 | 3.94 ± 0.03 | 0.78 ± 0.02 | 3.87 ± 0.04 | 0.78 ± 0.05 |
| Lying | 3.91 ± 0.03 | 3.92 ± 0.02 | 4.1 ± 0.04 | 3.87 ± 0.03 | 3.77 ± 0.04 | 4.12 ± 0.03 |

The data shows a large difference in the output on thigh and torso for a sitting subject and no significant difference between thigh and torso sensors for both standing and lying subjects. However, standing and lying are distinguished by the large difference in magnitude of the output for these positions. Thus, all three positions are distinguished by providing linked sensors, one on the torso and a second on the thigh.

The data shows that body position can be measured reliably using only accelerometers to perform the sagittal plane body position measurement; no magnetometers were needed to distinguish standing, sitting, and lying. This simplification allows elimination of orthogonal magnetometers, reducing system complexity, power demands, and potential errors associated associated with local variations in Earth's geomagnetic field. The magnetometers are only needed for measuring rotation or twist about an axis coincident with the gravity vector. They can be omitted to reduce cost complexity and power when measurement along such axis is not needed, as for the device to merely distinguish standing, sitting, and lying.

Figure 2A:
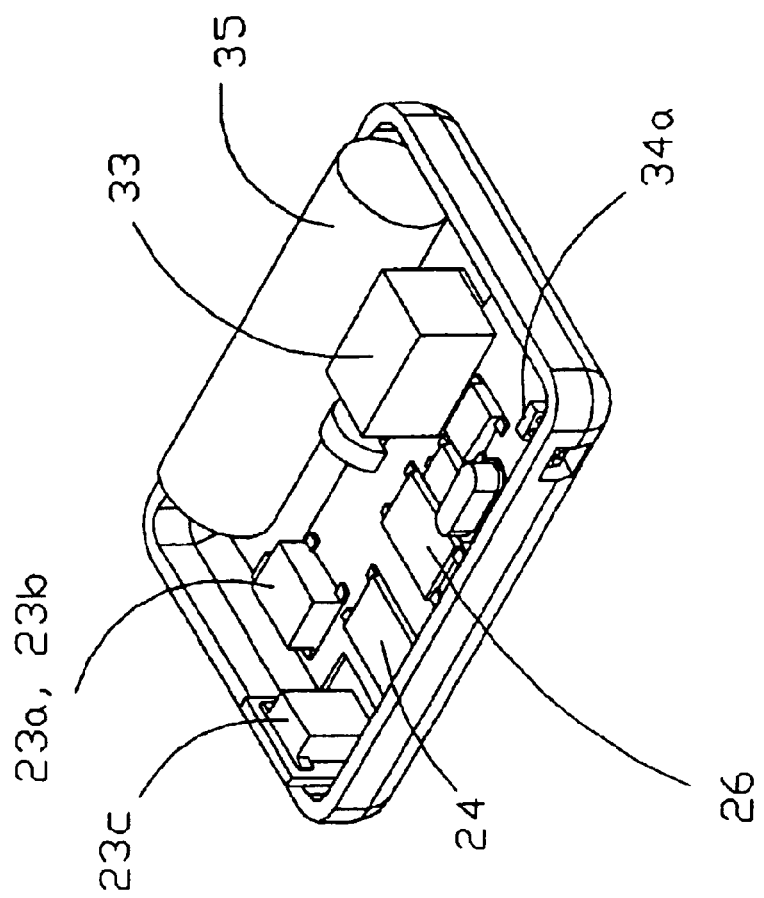
FIG. 2a is a three dimensional sensor unit of the present invention.

Preferably the accelerometers have a DC response, enabling measurement of steady state accelerations such as the gravity vector and inclination with respect to the gravity vector. The same accelerometers can also be used to determine linear velocity by integrating measured acceleration over time. A block diagram of sensor system unit 20a, shown in FIG. 1, includes inclinometer 22. Two or three orthogonal DC response accelerometers can be used to form the sensing portion of inclinometer 22. Accelerometers 23a, 23b, and 23c, shown in FIG. 2a, such as the ADXL202 (Analog Devices, Norwood, Mass.) have a DC response, offer very small package size and use extremely low power. The output of each accelerometer 23a, 23b, 23c is fed separately to low pass filter 24. The cutoff frequency of low pass filter 24 is typically set to ½ the sampling frequency for antialiasing. The output of low pass filter 24 is sent to the analog input of flash based microprocessor 26 (16F877 or 16C877 from Microchip Technology, Chandler, Ariz.) which includes analog to digital (A/D) converter 28. A flash based microprocessor has an on board flash memory for storing a program that will be run on the microprocessor. This on board flash memory plus additional non-volatile flash memory chip 30 are advantageous in that they allow for field reprogramming of the firmware without requiring replacement of the microprocessor chip. A crystal oscillator (not shown) in included with microprocessor 26 to control the timing of the microprocessor. Time is then determined in microprocessor 26.

In the embodiment of FIG. 1, all the requisite electronics, power, and packaging are contained in one sensor system 20a. Sensor system 20a also includes signal conditioning electronics 32, biofeedback mechanism 33 for providing feedback to the user, communications circuit 34a, internet interface 34b, power supply 35, and input button 36. Sensor system 20a can also include magnetometers or other sensors 38.

Microprocessor 26 samples the three accelerometers 23a, 23b, 23c (FIG. 2a) within inclinometer 22 at a sampling rate, such as 100 Hz. The data that was low pass filtered in hardware filter 24 will also be filtered in software run on microprocessor 26 using an Infinite Impulse Response (IIR) low pass digital filter that is formed in software to run on microprocessor 26. The IIR software filter allows very low cutoff frequencies to be achieved without using large components that would be required in hardware filters; and the filter can be made programmable by the user. Using both hardware and software filters provides additional noise reduction. Hardware low pass filter 24 also serves as an antialiasing filter, which is a filter that limits the frequency content of the sensor signal to a maximum frequency that is half the sample rate (100 Hz).

The device of the present invention employs at least one accelerometer based inclinometer 22 to measure the orientation of the wearer's body segments relative to earth's gravitational vector. In the preferred embodiment, accelerometers with a DC response are used to calculate angle so that information about the user in a quiescent state can be obtained and stored. If a triad of accelerometers 23a, 23b, 23c are used than an angle from +/−180 degrees can be measured on one axis relative to the gravity vector, and an angle range of +/−70 degrees can be measured on the other axis orthogonal to the first axis relative to the gravity vector, as shown in FIG. 3. The device uses microprocessor 26 that samples data from accelerometers 23a, 23b, 23c and calculates the angles $\theta_x$ and $\theta_y$ from equations 41–45 in FIG. 4a.

Offset and gain calibration coefficients $a_{xgain}$, $a_{ygain}$, $a_{zgain}$ used in equations 41–43 are stored in nonvolatile memory chip 30 on system 20a. Angles $\theta_x$ and $\theta_y$ so calculated are also stored in nonvolatile memory 30. Sampling is typically done at a frequency of 100 Hz but other sample frequencies can be programmed. The advantage of higher sampling frequency is that information about faster motions can be captured. The advantage of lower sampling frequency is that less data storage is needed.

$a_x$, $a_y$ and $a_z$ are calculated from the measured accelerometer sensor values along each axis, x, y, z, using equations 41, 42, 43, as shown in FIG. 4b. In the equation to calculate the acceleration along the x axis, ax, $a_{xraw}$ is the raw voltage reading from the x axis accelerometer. $a_{xoffset}$ is the offset coeficient to adjust the accelerometer for initial offset errors. $a_{xgain}$ is a coefficient to convert $a_{xraw}$ to a true acceleration reading. $A_{xgain}$ has units of g's per volt. Similar equations provide the y axis acceleration, $a_y$, and the z axis acceleration, $a_z$.

Rotations about the x and y axes are calculated in equations 44 and 45 by combining the accelerations calculated in equations 41, 42, and 43. Solid state accelerometers are well known in the art.

To measure rotations about the Z axis, magnetometers are required. The three orthogonal components of earth's magnetic field $m_x$, $m_y$ and $m_z$ are calculated from the measured values from magnetometers 38a, 38b, and 38c using using equations 71, 72, 73, as shown in FIG. 4b'. In the equation to calculate the magnetic field along the x axis, mx, $m_{xraw}$ is the raw voltage reading from the x axis magnetometer. $m_{offset}$ is the offset coeficient to adjust the magnetometer for initial offset errors. $m_{xgain}$ has units of Gauss per volt. Similar equations provide the my and mz values. From $m_x$, $m_y$, and $m_z$, $\theta_z$ can be calculated from equations 74, 75, 76, and 77 shown in FIG. 4c.

Accelerometers 23a, 23b, 23c are also used to calculate linear velocity. To determine the linear velocity the output of the hardware low pass filter is sampled at a rate of 100 Hz. To measure linear velocity, the portion of acceleration due to the gravity vector is eliminated using a high pass digital filter, which eliminates accelerations that remain constant. The high pass digital filtering is performed by microprocessor 26 using software stored on nonvolatile memory 30. The gravity vector is fixed at g, and therefore has a frequency of zero, so a high pass filter eliminates the gravity portion of the acceleration signal. As described herein above, the accelerometer data is scaled for offsets and gains and the magnitude of the resultant acceleration vector components $a_x$, $a_y$ and $a_z$ are computed, as described in equations 41, 42, and 43. While a uniform velocity cannot be measured with accelerometers, the time integral of the acceleration is computed using a digital numerical integration step to obtain the change in linear velocity vector resulting from acceleration.

Figure 5A:
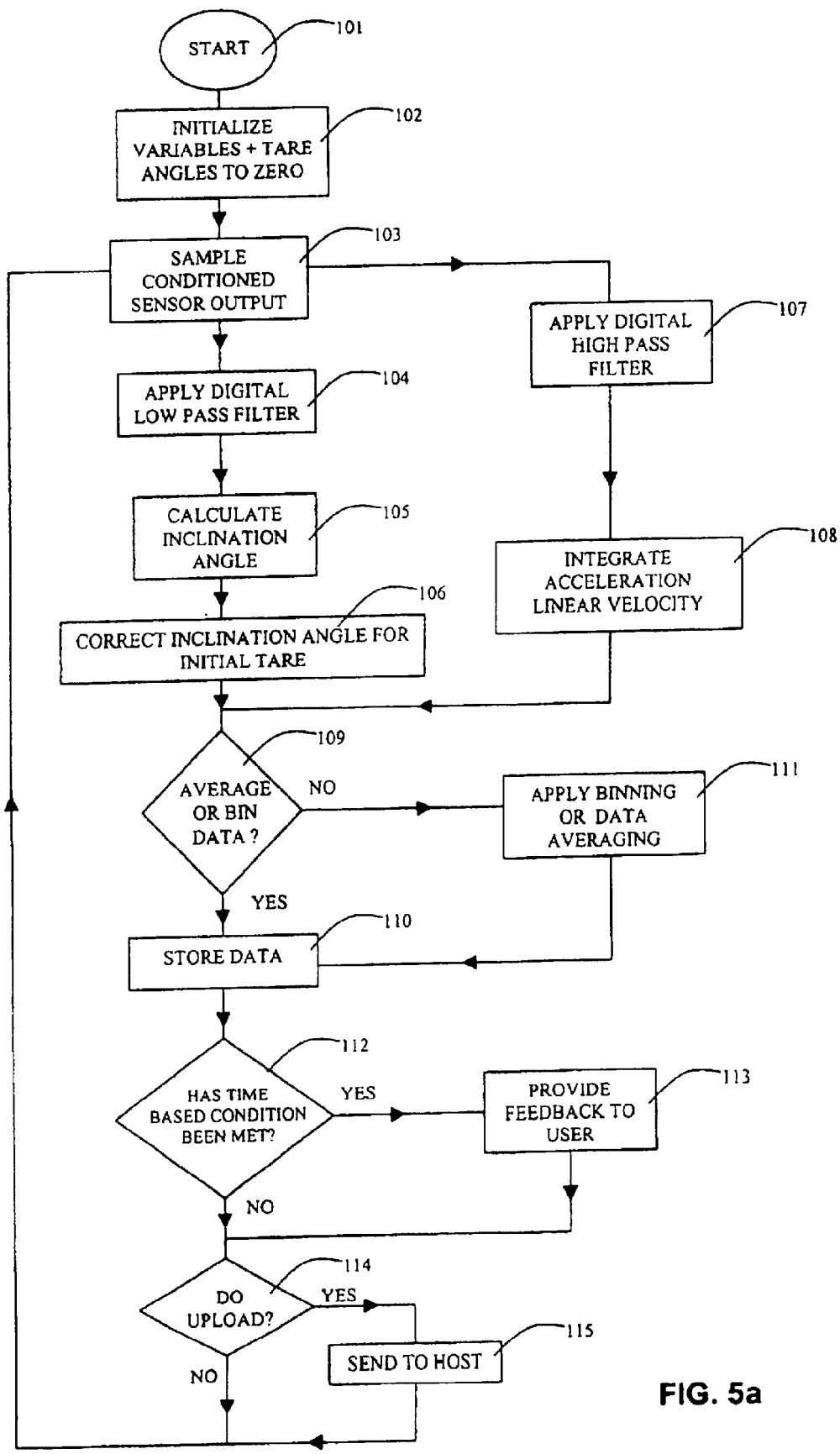
FIGS. 5a and 5b are flow charts showing two embodiments of the steps in the program run in the microprocessor of the apparatus.
Figure 5B:
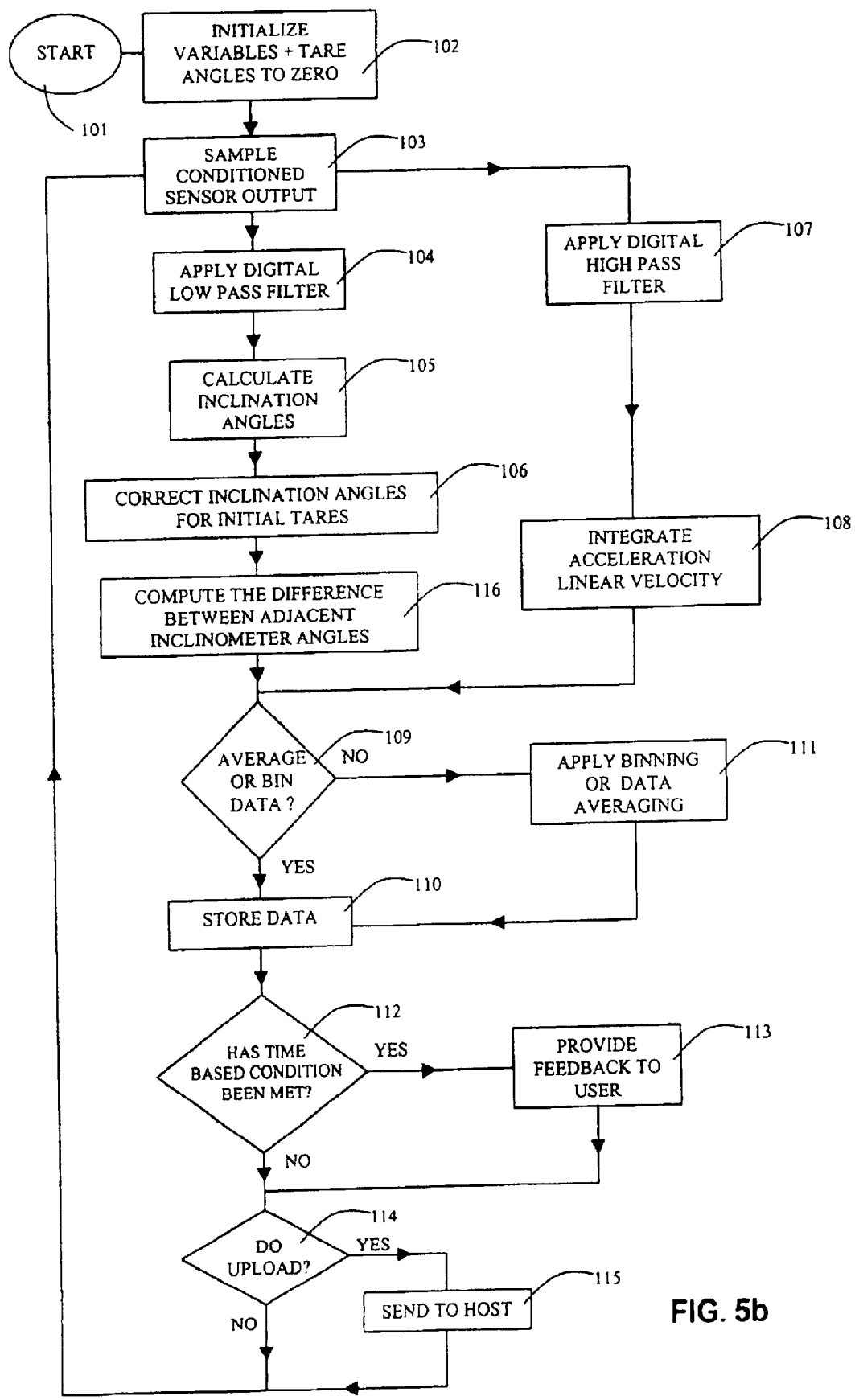

The results of the inclination and velocity calculations are stored in non-volatile flash memory 30 for each point in time as shown in the flow chart of FIG. 5 at box 110. This non-volatile memory chip 30 has the capability to store up to 4 megabytes of data on a single integrated circuit. The format of data storage in non-volatile flash memory 30 is programmable.

As an alternative to storing inclination and velocity at each point in time, the format of data storage can be programmed so the average of the inclination and velocity data over a programmable time period is stored at each interval of time, as shown in the flow chart of FIG. 5a at box

111. As another alternative, inclination angles and velocities can be segmented into bins and data accumulated in each bin as data is obtained at each point in time, as also shown at box 111. This provides histograms of the frequency of velocity and inclination angles over each time period. In this case, however, the sequential aspect of the information is removed.

Figure 6:
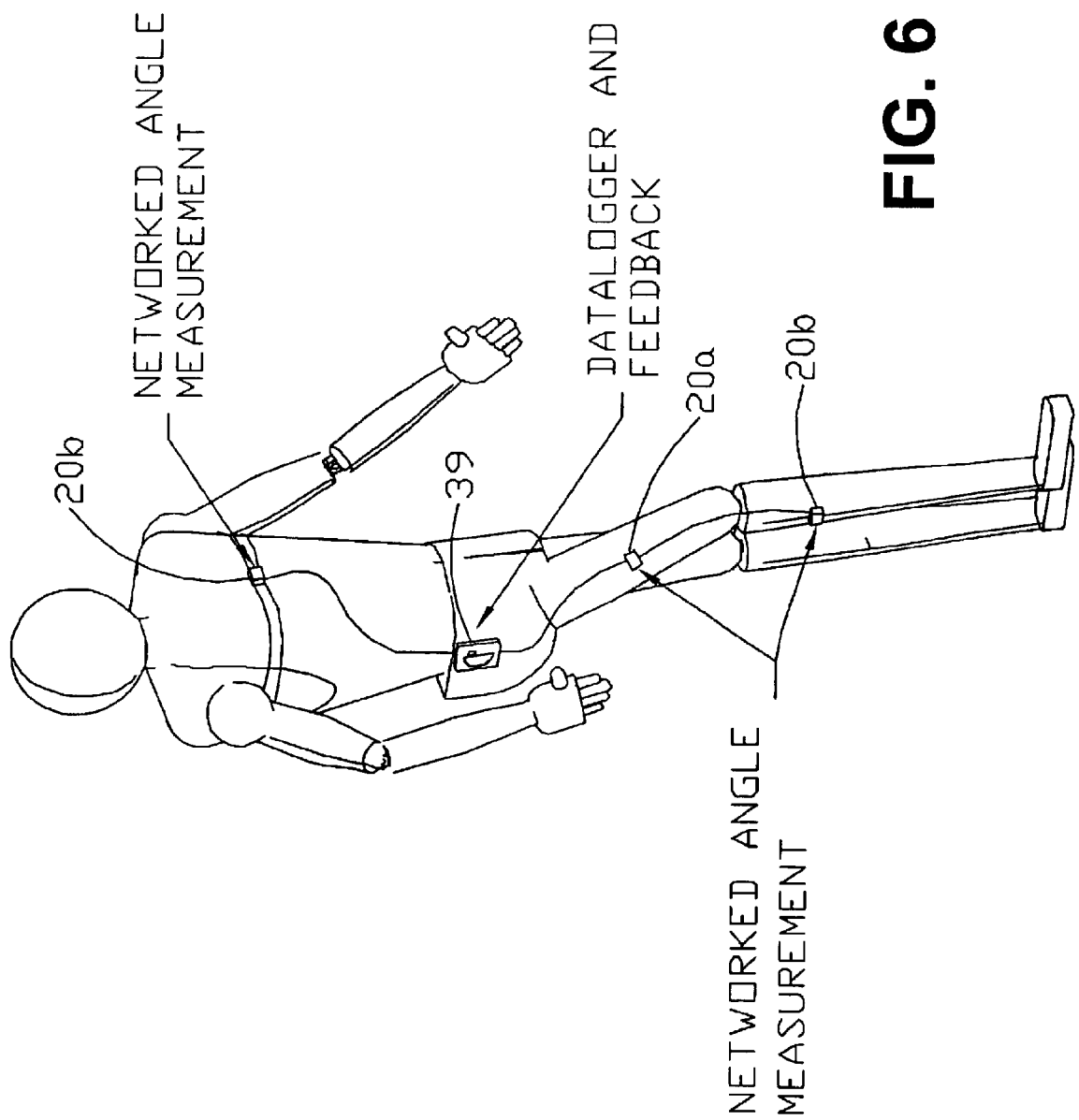
FIG. 6 is a three dimensional view of a person using a wire connected apparatus of the present invention.

Sensor system 20a can be located on one body segment, such as the lower trunk or the upper trunk, as shown in FIG. 6. A pair of sensor module units 20a, 20b can also be provided, one on each side of a joint, such as the hip joint. The difference between measurements of pair of sensor systems, 20a, 20b can be provided to detect angular position of the hip joint. Pairs of sensor systems 20a, 20b may be connected by wire 46 and connectors 48a, 48b, as shown in FIG. 1, or may use wireless communications, such as RF link 34a and antenna 49, also as shown in FIG. 1. The difference between the measurements of sensor systems 20a and 20b can be used to distinguish standing from sitting positions.

Pair of sensor systems, 20a, 20b can be provided to detect angular position of other joints in addition to or instead of the hip joint or to measure how that joint angle varies with time by taking the difference in the outputs of two sensor systems 20a, 20b, one on each side of the joint, as shown in FIG. 6 for a knee joint.

Where two or more sensor systems 20a, 20b are provided, sensor system 20b, need not have all the components of sensor system 20a, as shown in FIG. 1. Input button 36 to biofeedback mechanism 33 and internet interface 34b can be eliminated from slave sensor system 20b, since those functions can be provided by components in master sensor system 20a.

Inclinometers based on DC response accelerometers such as the ADXL202 (Analog Devices, Norwood, Mass.) have been described in commonly assigned U.S. patent application Ser. No. 08/990,912, herein by reference, and may be purchased commercially as FAS-A from MicroStrain, Inc., Burlington, Vt.

Sensors 20a preferably include accelerometer based inclinometers 22. They can also include magnetometers 38 to provide orientation around the gravity vector and to provide a complete orientation sensor. Orientation measurement devices that include magnetometers, such as the 3DM device of MicroStrain Inc., typically use both magnetometers and inclinometers to compute rotations coincident with the gravity vector. Such devices have been described in commonly assigned copending patent application Ser. No. 09/457,493.

Power may be supplied with battery power supply 35 that can be a battery, such as a miniature camera battery, and this battery can be rechargeable.

Biofeedback mechanism 33 can include a visual display capable of providing text or images or it can include a device that provides an audible signal, such as a piezoelectric buzzer, visual display, or a vibrator such as an electromagnetic shaker.

Figure 7:
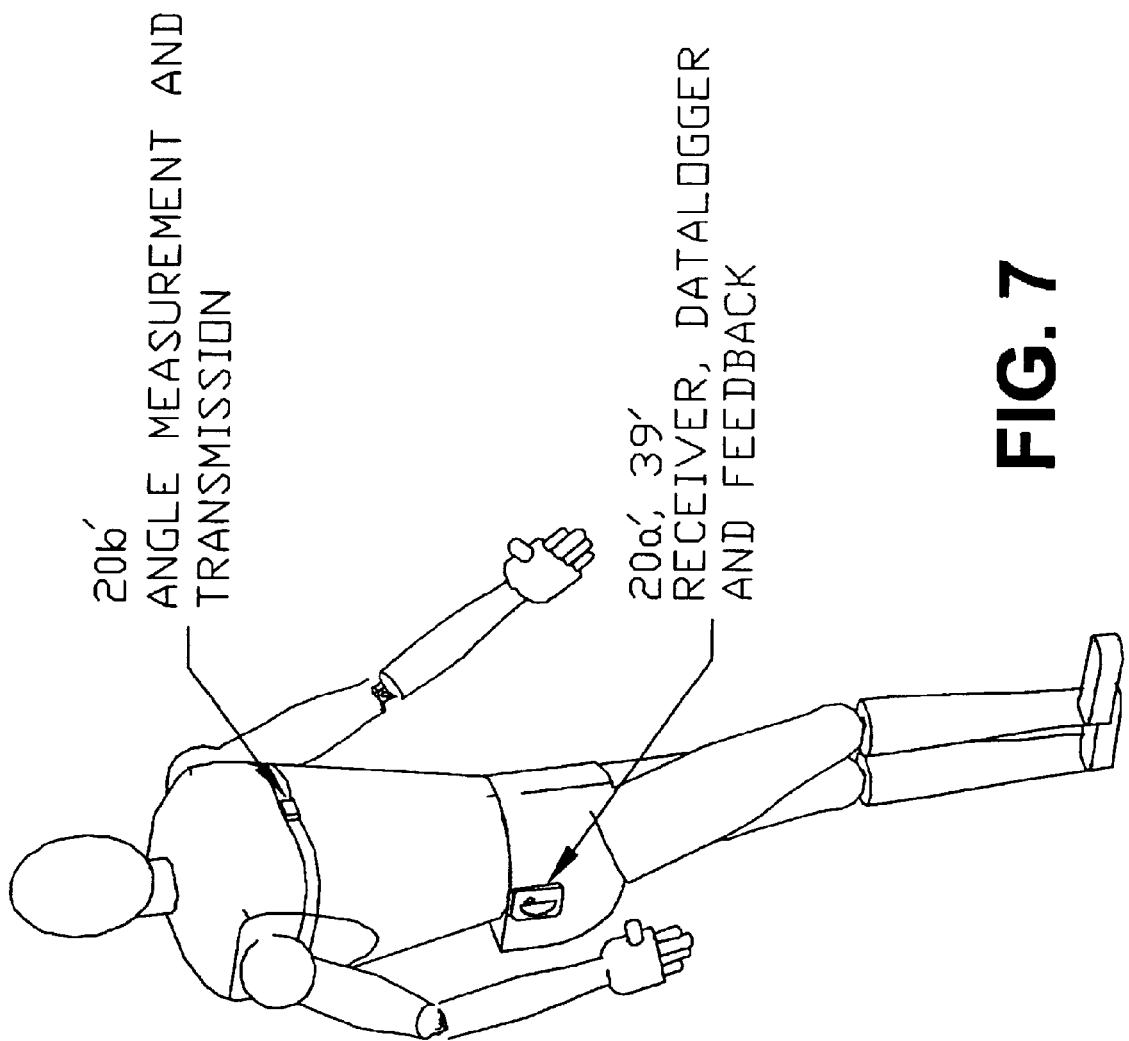
FIG. 7 is a three dimensional view of a person using a wireless apparatus of the present invention.

While biofeedback mechanism 33 can be included within sensor system 20a, as shown in FIG. 1, biofeedback mechanism 33 can be provided on a separate remote processing unit 39 that is used along with sensor system 20a, 20b, as shown in FIG. 6. This separate remote processing unit 39 (or wireless version 39') may be strapped to the user's waist, as shown in FIGS. 6 and 7, or it can mounted to another part of the user's body, such as the user's wrist, similar to a wristwatch, as shown in FIG. 9.

Figure 2B:
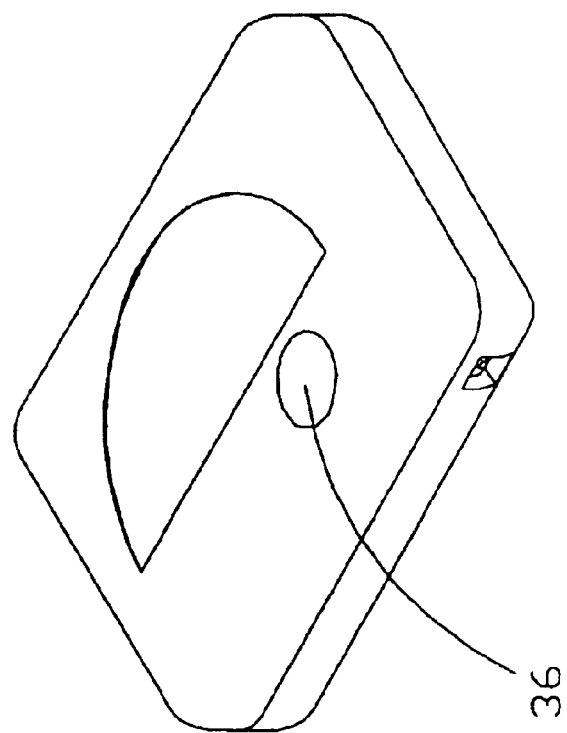
FIG. 2b is a three dimensional view of the sensor unit of FIG. 2a with the cover in place.

Feedback mechanism 33 and remote processing unit 39 can also provide for communication from a clinician treating patient as well as feedback based on the data collected by sensor system 20a as determined by the software program stored on nonvolatile memory 30 and run on microprocessor 26. Feedback mechanism 33 may also be combined with input unit 36, such as a single button or a keyboard, for the user to provide additional communication back to the clinician, as shown in FIG. 1 and in FIG. 2b. Thus, in addition to collecting data about the user's movement and posture for use by the internal program and for transmitting to the clinician, and for providing feedback, instructions, encouragement, or other display to the user, feedback mechanism 33 and remote processing unit 39 can also allow the user to let the clinician know when the user experiences pain or to communicate other information.

Data transmission between simplified sensor system 20b and remote processing unit 39 can be accomplished by hard wiring the two, as shown in FIG. 6. Preferably communication between simplified sensor system 20b' and remote processing unit 39' would be wireless, as shown FIGS. 7 and 8a-8c. In either the wired or wireless embodiments, each sensor system 20b, 20b' can be simplified somewhat to eliminate biofeedback mechanism 33, nonvolatile memory 30, input unit 36, and internet interface 34b since these can be provided in remote processing unit 39'. Simplified sensor system 20b, 20b' would now include measurement sensors, such as inclinometer 22, signal conditioners 32, filters 24, a/d converter 28, microprocessor 26, power supply 35 and communication mechanism 34a. Microprocessor 26 is provided with each sensor system 20a, 20a' 20b, 20b', so data is reduced to inclination or joint angle as a function of time and so the time dependent inclination or angle is transmitted in digital form.

The wireless version of communication mechanism 34a of FIG. 1 that is shown in FIG. 8a includes RF transmitter 50 (available from MicroStrain, Inc. Burlington, Vt.) for transmitting data from sensor system 20b' to remote processing unit 39' shown in FIG. 8b through RF transceiver 52 for remote data processing there in microprocessor 54. Remote processing unit 39' also includes data logging in non-volatile memory 56, biofeedback through biofeedback mechanism 58, and display 60, enabling the user to receive information, while power is provided to each of these components by power supply 62. Power supply 62 can be a small watch battery. Further transmission from remote processing unit 39' to host PC 64 is provided through RF transceiver 66, as shown in FIG. 8c.

Alternatively, RF transmitter 50 and transceivers 52 and 66 can be an infrared digital access (IRDA) link. In cases where line of sight is not practical then RF links would be employed. While wrist borne is convenient, remote processing unit 39' need not be wrist-borne; it can also be attached to the waist or to another convenient part of the body. It can also be held in a pocket, or strapped to another body part or it can also be hand held.

Wireless communication facilitates free range of motion, permits greater ease of use, enhances patient acceptance, has less potential for breakage due to lead wire fatigue, and is easier to integrate into garments such as bras or other unobtrusive strap-like apparel. Miniature wireless devices are available which contain the requisite electronics for digital transmission of data using narrow band surface acoustic wave (SAW) or crystal oscillators, such as Strain-Link™ modules available from MicroStrain, Inc.

Inclination data can be transmitted along with error checking from two separate sensors without RF collisions by using correctly configured Strainlink™ modules operating at different frequency transmission bands (such as 916 MHz and 303.825 MHz). Thus, data from a single pair of sensor systems 20a, 20b or 20a', 20b', formed of dual or triaxial accelerometers and mounted on adjacent limb segments can be used as shown in FIGS. 1 and 7. Alternatively, a plurality of sensor system 20b' can be simultaneously transmitted to remote processing unit 39', remotely processed there, and further transmitted to provide range of motion data to the clinician, as shown in FIG. 9.

Software capable of allowing remote re-programming of pre-set parameters is provided in non-volatile memory 56 of remote processing unit 39' for processing in microprocessor 54 in this unit (FIG. 8b). This is the same software described herein above that would otherwise be provided for each individual sensor system 20a, or 20a' for each pair of sensor systems, 20a, 20b or 20a', 20b' provided across a joint.

Sensor module system 20a, or 20a' or host system 64 could also incorporate a wired or wireless transmission system to allow for data transmission back to the clinicians' office without requiring the wearer to return to the office. In one embodiment the data is transmitted to receiver 66 and associated PC host 64 that is located in the patients' house. When all the data for the day has been acquired, host 64 would dial into the clinician's office and send the information over a modem or internet connection, as shown in FIG. 8C. This would all be transparent to the user. This would reduce the costs of administering the service significantly, by reducing the amount of time the clinician would have to see the patient. This would also allow for the clinician to view more data than would be possible if requiring the patient to come to the office could only retrieve data.

It is advantageous to implement the capability for the device to transfer data over the internet. With this capability it is possible for the patient to transfer data to the clinician's office without requiring the physical presence of the patient. It also would allow for the device to be updated and change parameter's, such as allowable range of motion before a warning is triggered.

Remote processing unit 39' includes display 60 that may provide simple text commands. Display 60 could also provide graphical representations of people doing various movements to communicate the desired information or instruction to the user. The graphical display allows for the display of a score, helps teach good posture, and helps the user through exercises. Remote processing unit 39' can also be used to perform mathematical computation of joint angles. It can be the unit that uses the data to conclude that a preset limit to range of motion had been exceeded too many times, that the subject has been too sedentary. Once the data from sensor system 20a, 20a', 20b, 20b' has been received and interpreted by wrist-borne remote processing unit 39 this unit could also provide feedback to the user using a vibrational, audible, or visual signal.

When preset or remotely programed conditions are detected, such as movement extending beyond a preset range of motion, the user is provided feedback as shown in box 113 of the flow chart in FIG. 5a. Feedback can be negative feedback seeking to halt or reverse that motion. When the user performs a requested task well or indicates improvement in compliance with program requests, the user may be provided positive feedback, such as a higher "health" score. These conditions, programs, displays, and interactions can all be programmed by the clinician (at the office or remotely) depending on the user's behavior or the clinician's expert assessment of the user's progress.

In addition to providing a biofeedback signal, it is advantageous to continually save information about the user's range of motion, which may be changing with time. This allows the clinician to evaluate rehabilitation progress. In addition, stored information provides a valuable research tool to study how movement or lack of movement may correlate with low back pain, cardiac ailments, dietary modifications, pharmacological treatments, and postural control.

Data can be saved as inclination angle at each time. It can be saved more compactly in histograms; each histogram's sum represents the total count of trunk inclination angles measured at the programmed sample rate (binning frequency). While more data can be stored in histogram format, the association with time of each individual by data point and the time sequence is lost. Binned data are very useful in reducing the datalogger's requisite memory; once collected, these histogram data are easily downloaded over the serial port of microprocessor 26 on sensor system 20a or microprocessor 54 within remote processing unit 39' for analysis. The device logs inclination in 1 degree increments (factory set, but may be programmed) over ±180 in the flexion extension axis and ±70 degrees on the lateral bending axis. The sample rate for data collection is termed the binning frequency; as data is collected, the unit builds a histogram of inclination over specified time intervals (bin save interval) and then saves this histogram to memory. The process is repeated until the device is turned off or the memory capacity is reached. The data and programming parameters are saved in non-volatile memory, and will not be lost in the event of power down or low battery capacity.

The bin save interval can be programmed for any amount of time, but longer intervals provide lower resolution of the wearer's activity. For example, if the bin save interval were set at one hour, at the end of the day there would be 24 histograms showing the wearer's trunk inclination angle at the period of the binning frequency. This would show a histogram of inclination for each hour over the course of a day. If the bin save interval were set at 12 hours, at the end of a day there would be only 2 histograms of inclination. Longer bin save intervals use less memory than shorter bin save intervals, but longer bin save intervals provide less information about daily activities. The advantage of binning over saving data sequentially over time is that binning uses less memory.

Binned data has been collected and presented in a paper, "Evaluation of Biofeedback Device in Reducing Pain and Improving Function of Individuals with Low Back Pain," by M. H. Krag, J. R. Fox, and L. P. McDonald, *Rehabilitation Society of N. America*, Pittsburgh, Pa., 1997.

Binning of data saves memory but the sequential recording of events is lost with binning. This is a limitatioon when repetitive motions of activities need to be recorded or when continuous exposure to a single posture or position or vibration occurs. In these cases the product of position and time is a measure of a person's exposure to that position. The repeated pattern of movement may also be important to asess exposure in a workplace environment. This analysis requires that postural and motion measurements be recorded sequentially and along with the time of the measurement. FIG. 5a provides a flow chart detailing this sequential recording of data.

The user can record events (such as the presence of pain) with input button 36 which can be included either in sensor system 20a or on remote processing unit 39. Button 36 can also be on wrist-borne remote processing unit 39' to conveniently allow the wearer to provide this input when experiencing pain. When button 36 is pressed, the time may be logged and stored in the system, along with other data, such as time of day, inclination, orientation, heart rate, blood pressure, etc. This system of measurements and data communications will allow the clinician to gain insight into the pain the user has experienced along with a chronological history of the ranges of motion and activities the patient experiences leading up to the onset of pain. If a correlation can be determined, the clinician can program the biofeedback to try to discourage the wearer from performing events that led to pain. This feature may be especially important for back pain sufferers, since they often experience pain well after the physical activities that may have caused the pain.

Accelerometers 23a, 23b, 23c used to sense inclination angle can also be used to sense the vibration that the user is experiencing. For example, for a worker using a jack hammer or a chain saw, the device of the present invention will measure the vibration, log the vibration exposure dose received by the worker over time, and then give feedback if this worker receives more vibration dose than a preset vibration exposure dose. The frequency and magnitude of the vibrations is determined by calculating fast fourier transforms (FFT) of the acceleration data coming from the accelerometers or logged in memory. This FFT data is logged, and feedback can be provided based on the magnitude, frequency, and time history of the calculated vibrations. It is well known how to do a FFT, and the algorithm to transform a time domain signal to a frequency domain signal is also well known.

Variables can be initialized and initial readings can also be tared out as shown in box 102 of FIG. 5a. The sensor is initialized to a known angle, such as zero, before the first measurement is taken. This is especially useful for postural control applications, since the user may tare the device at a desired position, regardless of slight variations that may result from various mountings to the wearers' body.

The wearer places a miniature sensor module package 20a, 20a' in a small pouch located in their bra, or bra-like device on the chest or on the wrist. This miniature sensor module package 20a, 20a' contains inclinometer 22 with vibratory biofeedback capability. The user then stands in front of a mirror to better view his or her own posture. Once a desirable physical appearance or a comfortable posture, or both, is achieved, the user initializes or "tares" the unit. When the user exceeds a pre-programmed inclination angle (in this case, say 2 degrees), the user experiences vibratory or other feedback from the feedback mechanism 33 as shown in the flow chart in box 113 of FIG. 5a. If the subject is undergoing vigorous physical range of motions (such as sit-ups or other flexion type exercise), the unit interprets these patterns and does not provide feedback so as not to annoy the wearer during exercise.

In addition to magnetometers, the present invention also provides for data to be collected and monitored from other sensors 38 such as force measurement sensors, temperature, electrocardiogram (ECG/EKG), electromyograph (EMG), and lumbar curvature, as shown in FIG. 1.

While several embodiments of the invention, together with modifications thereof, have been described in detail herein and illustrated in the accompanying drawings, it will be evident that various further modifications are possible without departing from the scope of the invention. Nothing in the above specification is intended to limit the invention more narrowly than the appended claims. The examples given are intended only to be illustrative rather than exclusive.

What is claimed is:

1. A device for attaching to a living subject having a joint, comprising a first sensor, a second sensor, a processor, and a non-volatile storage device, said first sensor for attaching to a first body segment above the joint, said second sensor for attaching to a second body segment below the joint, wherein said first sensor and said second sensor each comprise a solid state inclination measuring device for determining inclination with respect to the gravity vector, wherein said inclinations with respect to the gravity vector determined from said first sensor and from said second sensor are processed in said processor and stored in said non-volatile storage for distinguishing lying, sitting, and standing positions, wherein said processor and said non-volatile storage device are part of the device for attaching to the living subject.

2. A device as recited in claim 1, wherein said inclination measuring device comprises a dc accelerometer.

3. A device as recited in claim 1, wherein said inclination measuring device comprises three accelerometers orthogonally mounted.

4. A device as recited in claim 1, wherein said inclination measuring device further comprises a magnetometer.

5. A device as recited in claim 1, wherein said inclination measuring device comprises a plurality of magnetometers.

6. A device as recited in claim 5, wherein data from said magnetometers is for providing direction with respect to the earth's magnetic field.

7. A device as recited in claim 1, wherein data from said first sensor is subtracted from data from said second sensor.

8. A device as recited in claim 7, wherein said subtraction is to determine a difference in orientation.

9. A device as recited in claim 7, wherein said first sensor and said second sensor are for measuring range of motion of said second body segment with respect to said first body segment.

10. A device as recited in claim 9, wherein data from said range of motion measurement is analyzed for change of range of motion over time.

11. A device as recited in claim 10, wherein initial values of said time dependent data are tared out to provide change from said initial values.

12. A device as recited in claim 1, wherein said non-volatile storage device comprises a solid state device.

13. A device as recited in claim 12, wherein said non-volatile storage device comprises a non-volatile memory chip.

14. A device as recited in claim 1, further comprising a feedback mechanism.

15. A device as recited in claim 14, further comprising a housing, wherein said first sensor, said storage device, said processor, and said feedback mechanism are all within said housing.

16. A device as recited in claim 14, further comprising a housing separate from said first sensor and said second sensor, wherein said feedback mechanism is within said housing.

17. A device as recited in claim 16, wherein said first sensor and said second sensor are wirelessly connected to said housing containing said feedback mechanism.

18. A device as recited in claim 17, wherein said wireless connection is an RF connection.

19. A device as recited in claim 14, wherein said processor is programmed to activate said feedback mechanism if a preset range of motion threshold has been exceeded more than a specified number of times.

20. A device as recited in claim 14, wherein said feedback mechanism includes a vibrator.

21. A device as recited in claim 14, wherein said feedback mechanism comprises a piezo-electric buzzer or an electromagnetic shaker.

22. A device as recited in claim 14, wherein said feedback mechanism includes a vibratory or audio signal to provide feedback to provide one or more of the following; warn of a problem, discourage a movement, support a desired result, and encourage a movement.

23. A device as recited in claim 22, wherein said processor is programmed to provide feedback if the living subject repeatedly exceeds a pre-programmed inclination angle.

24. A device as recited in claim 1, wherein said processor comprises a microprocessor, a signal processor, or a personal computer.

25. A device as recited in claim 1, wherein data from said inclination determination comprises body segment inclination data as a function of time.

26. A device as recited in claim 1, wherein data from said inclination determination comprises posture date as a function of time.

27. A device as recited in claim 1, further comprising an output to provide data from said inclination determination for use to adjust physical therapy.

28. A device as recited in claim 1, wherein said device further comprises a data entry system.

29. A device as recited in claim 28, wherein said data entry system comprises a button.

30. A device as recited in claim 28, wherein said data entry system includes an input unit for recording the presence of pain.

31. A device as recited in claim 28, wherein one or more of the following data are recorded when said data entry system is used; time, date, and other data.

32. A device as recited in claim 1, further comprising a program for displaying data from said inclination determination as a histogram showing number of inclinations at each angle range during a time period.

33. A device as recited in claim 1, further comprising a program for displaying data from said inclination determination as inclination v time.

34. A device as recited in claim 1, further comprising a digital filter.

35. A device as recited in claim 34, wherein said device may be subject to linear accelerations, wherein said digital filter is for reducing effect of said linear accelerations on the data.

36. A device as recited in claim 34, wherein said digital filter comprises a low pass filter or a high pass filter.

37. A device as recited in claim 1, wherein said inclination measuring device comprises dc accelerometers, wherein said device further comprises a high pass filter, wherein output of said accelerometers that passes through said high pass filter is subsequently integrated and used to compute a resultant velocity which is used to calculate energy used.

38. A device as recited in claim 1, wherein said processor uses inclination data from said first and second sensors for determining body posture in said sitting position.

39. A device as recited in claim 1, wherein said joint is a hip joint.

40. A device as recited in claim 1, further comprising a sensor for further detecting posture based on curvature of the spine.

41. A device as recited in claim 40, wherein said sensor is capable of detecting a kyphotic curvature of the spine.

42. A device as recited in claim 41, wherein said processor is programmed to measure the time the subject has said kyphotic curvature of the spine and determines whether said time exceeds a preset value, and wherein said processor is further programmed to prompt the subject to move if said time exceeds said preset value.

43. A device as recited in claim 1, wherein said processor uses inclination data from said first and second sensors for distinguishing bending in one said position.

44. A device as recited in claim 1, wherein said processor uses inclination data from said first and second sensors for distinguishing forward bending, backward bending, and lateral bending.

* * * * *